(12) United States Patent
Hutchings et al.

(10) Patent No.: US 8,901,028 B2
(45) Date of Patent: Dec. 2, 2014

(54) SELECTIVE HYDROCARBON OXIDATION USING HETEROGENOUS CATALYSTS

(75) Inventors: Graham John Hutchings, Ross on Wye (GB); Jose Antonio Lopez-Sanchez, Liverpool (GB); Ceri Hammond, Cymru (GB); Nikolaos Dimitratos, Oxford (GB); Nicholas Fracois Dummer, Cardiff (GB)

(73) Assignee: University College Cardiff Consultants Limited, Wales (GB)

( * ) Notice: Subject to any disclaimer, the term of this patent is extended or adjusted under 35 U.S.C. 154(b) by 0 days.

(21) Appl. No.: 13/639,921

(22) PCT Filed: Jun. 25, 2010

(86) PCT No.: PCT/ES2010/070431
§ 371 (c)(1),
(2), (4) Date: Oct. 8, 2012

(87) PCT Pub. No.: WO2011/161276
PCT Pub. Date: Dec. 29, 2011

(65) Prior Publication Data
US 2013/0090495 A1 Apr. 11, 2013

(51) Int. Cl.
*B01J 23/00* (2006.01)
*C01F 7/00* (2006.01)
*C07C 51/285* (2006.01)
*C07C 407/00* (2006.01)
*C07C 29/48* (2006.01)

(52) U.S. Cl.
CPC .............. *C07C 51/285* (2013.01); *C07C 407/00* (2013.01); *C07C 29/48* (2013.01)
USPC .......................................... 502/316; 423/716

(58) Field of Classification Search
USPC .......................................... 502/316; 423/716
See application file for complete search history.

(56) References Cited

U.S. PATENT DOCUMENTS

| 5,021,607 | A | 6/1991 | Huybrechts |
| 5,126,491 | A * | 6/1992 | Clerici et al. ................. 568/342 |
| 5,830,429 | A | 11/1998 | Balkus, Jr. et al. |
| 2006/0094905 | A1 | 5/2006 | Deshpande et al. |
| 2012/0201743 | A1 | 8/2012 | Chadwick et al. |
| 2012/0203035 | A1 | 8/2012 | Lopez-Sanchez et al. |

OTHER PUBLICATIONS

Appl. Catal. A 247 (2003) 269.
B. Michalkiewicz et al., J. Catal. 215 (2003) 14.
Busca, Chem. Rev., 107 (2007) 5366.
E.D. Park et al., Catal. Commun. 2 (2001) 187.
G.J. Hutchings, et al., Science, 323 (2009) 5917, 1037-1041.
Khouw, Journal of Catalysis, 1994, vol. 149, p. 195-205.
L. Chen et al., Energy and fuels, 20 (2006) 915.
Raja, et al., Applied Catalysis A: General, 158 (1997) L7.
Shul'pin, et al., Tetrahedron Letters, 47 (2006) 3071.
Sorokin, et al., Chem. Commun., (2008) 2562.
Yuan, et al., Adv. Synth. Catal. 349 (2007) 1199.
PCT/ES10/070431, International Search Report and Written Opinion.
PCT/ES10/070431, International Preliminary Report on Patentability.
PCT/ES10/070431, Response Written Opinion.
PCT/ES2011/070064, International Search Report and Written Opinion.
PCT/ ES2011/070064, Response Written Opinion.

\* cited by examiner

*Primary Examiner* — Nizal Chandrakumar

(57) ABSTRACT

A process for the complete or partial oxidation of hydrocarbons comprises contacting a $C_1$-$C_8$ hydrocarbon and hydrogen peroxide in the presence of a heterogeneous catalyst under conditions suitable to convert the $C_1$-$C_8$ hydrocarbon to at least one corresponding $C_1$-$C_8$ oxygenate product, wherein the heterogeneous catalyst provides confinement and contains both Brønsted-Lowry and Lewis acid centers. Particularly useful catalysts may include, for example, metal-modified ZSM-5 and other zeolites.

9 Claims, No Drawings

SELECTIVE HYDROCARBON OXIDATION USING HETEROGENOUS CATALYSTS

BACKGROUND

1. Field of the Invention

This invention relates to processes and catalysts that convert $C_1$-$C_8$ hydrocarbons to corresponding partially oxygenated compounds, such as methane to methanol, using heterogeneous catalysts.

2. Background of the Art

Activation and oxidation of lower alkanes ($C_1$-$C_8$) into useful oxygenates has long been an attractive and challenging research area. One reason for this interest is the fact that lower alkanes, especially methane ($CH_4$) and ethane ($C_2H_6$), are predominant constituents of natural gas, which is currently both abundant and inexpensive. However, activation of lower alkanes often requires severe conditions using heterogeneous catalysts, for example, a temperature greater than 500 degrees Celsius (° C.) combined with increased pressure. Under these reaction conditions the valuable oxygenate products are, unfortunately, not stable, and the formation of carbon oxides, such as carbon monoxide (CO) and carbon dioxide ($CO_2$), is usually observed.

In view of this problem, it is generally considered to be desirable to work at milder conditions, such that the formation of CO and/or $CO_2$ is reduced or eliminated and the stability of the oxygenate products formed is enhanced. To enable these milder conditions, some researchers have explored activation of $CH_4$ in the liquid phase, instead of in the gas phase. For example, B. Michalkiewicz, et al., *J. Catal.* 215 (2003) 14, reports the oxidation of $CH_4$ to organic oxygenates at 160° C. and a $CH_4$ pressure of 3.5 megapascals (MPa), using metallic palladium dissolved in oleum. That reference claims that methanol is obtained by the transformation of the $CH_4$ to methyl bisulfate and dimethyl sulphate, and the ester is subsequently hydrolyzed. Unfortunately, use of strong acidic media such as sulfuric acid involves corrosive, toxic reaction conditions and a large amount of waste. Other research using oleum is reported in L. Chen, et al., *Energy and Fuels,* 20 (2006) 915, wherein vanadium oxide ($V_2O_5$) in oleum is employed, at 180° C. and a $CH_4$ pressure of 4.0 MPa.

Mild conditions are also used in E. D. Park, et al., *Catal. Commun.* 2 (2001) 187, and *Appl. Catal. A* 247 (2003) 269, wherein selective oxidation of $CH_4$ is carried out using hydrogen peroxide generated in situ, using a palladium/carbon (Pd/C) and copper acetate ($Cu(CH_3COO)_2$) catalyst system, with trifluoroacetic acid (TFA) and trifluoroacetic anhydride (TFAA) as solvents. The Pd/C serves as an in situ generator of hydrogen peroxide ($H_2O_2$), while the $Cu(CH_3COO)_2$ serves as the oxidation catalyst. The reaction conditions disclosed include 80° C., 5 mL solvent and a total gas pressure of 47.64 standard atmospheres (atm) (4.83 MPa) (71.4 percent (%) $CH_4$, 14.3% hydrogen ($H_2$), 14.3% oxygen ($O_2$)). This process, too, requires formation of an ester followed by subsequent hydrolysis, and thus is not direct.

A method involving direct conversion of $CH_4$ to oxygenate products is disclosed in Qiang Yuan, et al., *Adv. Synth. Catal.* 349 (2007) 1199, wherein $CH_4$ is oxidized in an aqueous medium using $H_2O_2$ and homogeneous transition metal chlorides as catalysts. The transition metal chlorides may include, for example, iron chloride ($FeCl_3$), cobalt chloride ($CoCl_2$), ruthenium chloride ($RuCl_3$), rhodium chloride ($RhCl_3$), palladium chloride ($PdCl_2$), osmium chloride ($OsCl_3$), iridium chloride ($IrCl_3$), platinum hydrochloride ($H_2PtCl_6$), copper chloride ($CuCl_2$), and gold hydrochloride ($HAuCl_4$). Unfortunately, in this process recovery and reuse of the homogeneous catalyst is difficult at best.

Other researchers have also addressed the use of microstructured catalysts. For example, Raja, et al., *Applied Catalysis A: General,* 158 (1997) L7, discloses a process to oxidize $CH_4$ to methanol using phthalocyanine complexes of iron (Fe) and copper (Cu) encapsulated in zeolites as catalysts, and a combination of oxygen ($O_2$) gas and tert-butyl hydroperoxide, which is in aqueous solution, as oxidants. The process includes an autoclave reactor and a suitable solvent, such as acetonitrile, and is carried out with the tert-butyl hydroperoxide at 273 degrees Kelvin (K) (0° C.) and a reaction time of 12 hours (h). The products include methanol, formaldehyde, formic acid and $CO_2$.

Shul'pin, et al., *Tetrahedron Letters,* 47 (2006) 3071, discloses a process for the oxidation of alkanes (including $CH_4$, $C_2H_6$, propane, n-butane, hexane, heptane, octane and nonane) using $H_2O_2$ as the oxidant to form the corresponding alcohols and ketones. The process includes an autoclave reactor with, in the case of $CH_4$, a pressure of 50 bar (5 MPa) and a reaction time of 24 h. The catalyst is a titanium-containing zeolite, "TS-1" (silicon (Si) to titanium (Ti) ratio is 20, Si/Ti=20), and methanol is the main product (1.1 micromole (µmol) of methanol produced after 24 h).

Finally, Sorokin, et al., *Chem. Commun.,* (2008) 2562, discloses the oxidation of $CH_4$ under mild conditions (25-60° C., 32 bar (3.2 MPa) $CH_4$ pressure, 678 µmol $H_2O_2$, and a reaction time of 20 h) using a µ-nitrido diiron phthalocyanine complex in water as a homogeneous catalyst and, additionally, a silica-supported µ-nitrido diiron phthalocyanine complex. The products include methanol, formaldehyde and formic acid, with formic acid being primary.

While researchers have identified a number of operable processes, there is still a need to identify additional processes that are both environmentally benign and economically attractive, and that desirably do not require intermediate steps or products in order to produce the desired final oxygenate products from $C_1$-$C_8$ hydrocarbons.

SUMMARY OF THE INVENTION

In one embodiment the invention provides a process for the complete or partial oxidation of hydrocarbons, comprising contacting a $C_1$-$C_8$ hydrocarbon and hydrogen peroxide in the presence of a heterogeneous catalyst under conditions suitable to convert the $C_1$-$C_8$ hydrocarbon to at least one corresponding $C_1$-$C_8$ oxygenate product, wherein the heterogeneous catalyst provides confinement and contains both Brønsted-Lowry acid centers and Lewis acid centers.

DETAILED DESCRIPTION OF THE EMBODIMENTS

The invention, in one aspect, is a process for forming an oxygenate product from a hydrocarbon, such as methanol from $CH_4$. The process involves contacting a $C_1$-$C_8$ hydrocarbon and hydrogen peroxide, in the presence of a heterogeneous catalyst, in gas phase, condensed phase, or a combination thereof under the selected process conditions, in order to convert the $C_1$-$C_8$ hydrocarbon to at least one of its corresponding $C_1$-$C_8$ oxygenate products. By "corresponding" is meant an oxygenate product having the same number of carbon atoms as the $C_1$-$C_8$ hydrocarbon being oxidized. The $C_1$-$C_8$ hydrocarbon may be saturated or unsaturated, cyclic or linear, or any combination thereof. In one embodiment the hydrocarbon is $CH_4$; in another embodiment it is $C_2H_6$; in still another embodiment it is cyclohexane; and in yet another embodiment it is octane. Mixtures of hydrocarbons may also be selected. The hydrocarbon is desirably selected according to the target final oxygenate product(s), which may be, e.g., an alcohol, an alkyl peroxide, an aldehyde, a carboxylic acid, or a combination thereof. For example, if the desired final oxygenate product is methanol, methyl-hydroperoxide, formaldehyde and/or formic acid, the selected hydrocarbon would desirably be $CH_4$.

The second starting material in the conversion of the $C_1$-$C_8$ hydrocarbon is hydrogen peroxide ($H_2O_2$). This $H_2O_2$ may be supplied as a discrete reagent, for example, obtained from a commercial supplier as an aqueous solution or in concentrated form, or received in concentrated form and then diluted onsite with additional water or another suitable solvent such as, for example, methanol. In another embodiment, it may be generated in situ, in the same reaction medium and essentially concurrently with the conversion of the $C_1$-$C_8$ hydrocarbon. Where it is desired to generate the $H_2O_2$ in situ, such is most effectively accomplished by contacting a source of hydrogen and a source of oxygen. Any sources of hydrogen and oxygen may be used in the process of this invention, but in order to reduce undesirable side reactions and/or formation of undesirable by-products, use of hydrogen gas ($H_2$) and oxygen gas ($O_2$), for example, by using air as the source of $O_2$, may be particularly convenient. Hydrogen obtained from the dehydrogenation of hydrocarbons and alcohols may also be used, especially if such is conveniently available and inexpensive.

The third required material is a catalyst. Such is, by definition, heterogeneous, meaning that it is not soluble in the $C_1$-$C_8$ hydrocarbon being converted, whether such hydrocarbon is in liquid phase, gas phase, or a combination thereof. The catalyst is further defined as containing both Brønsted-Lowry and Lewis acid centers. The nature of acid centers, and therefore identification of such centers as being of either the Brønsted-Lowry type or the Lewis-type, may be defined using any of several conventional methodologies. Among these are, for example, Temperature Programmed Desorption of Ammonia (TPD-$NH_3$); Infrared (IR) spectroscopy, based on either pyridine or $NH_3$; and Proton Magic Angle Spinning Nuclear Magnetic Resonance ($^1$H-MAS NMR), which is described in, for example, G. Busca, *Chem. Rev.*, 107 (2007) 5366, incorporated herein by reference in its entirety.

Using such methodologies, a "Brønsted-Lowry acid center" is identified as a hydrogen ion, i.e., a proton, that is donated by the catalyst to a reaction intermediate in the inventive process's primary oxidation reaction, i.e., the oxidation of the $C_1$-$C_8$ hydrocarbon to form an oxygenate product. Determination of whether a given solid catalyst candidate donates a proton in a reaction may be carried out by, for example, IR spectroscopy, wherein a pyridine is made available for adsorption by the catalyst candidate. The presence of a Brønsted-Lowry acid center is confirmed if vibrations corresponding substantially to 1640, 1628, 1544, and 1492 $cm^{-1}$ are recorded. These measurements represent a protonated pyridine complex, which means that a pyridinium ion has been formed, indicating the presence of a Brønsted-Lowry acid center in the catalyst.

A "Lewis acid center" is identified as a coordinatively-unsaturated metal cation. As used herein, the phrase "coordinatively-unsaturated metal cation" means that the catalyst contains a metal cation that is capable of forming a coordination complex with an available ligand. In the primary oxidation reaction of the inventive process, the coordinatively unsaturated metal cation, for example, an aluminum ($Al^+$) or iron ($Fe^+$) cation having a low-lying vacant orbital, can serve as an electron acceptor. Determination of whether a given solid catalyst candidate accepts one or more electrons in a reaction may be carried out by, for example again, IR spectroscopy, wherein a pyridine is made available for adsorption by the catalyst candidate. The presence of a Lewis acid center is confirmed if vibrations corresponding substantially to 1624, 1618, and 1597 $cm^{-1}$ are recorded. These vibrations are attributed to three different coordinatively complexed pyridine species, which means that a coordinative metal cation is present in the catalyst. Such coordinative metal cation is, by definition, a Lewis acid center.

It is notable that, in the catalysts that are useful in the inventive process, both Lewis and Brønsted-Lowry acid centers are present. Such may be both located on the surface of the catalyst, or, in the case of, for example, some types of porous crystalline catalysts, the Lewis acid centers may be located primarily on the exterior surface, while the Brønsted-Lowry acid centers may be located primarily in the interior of the pores. Alternatively, Lewis acid centers may be added to a catalyst that, in its as-synthesized form, contains only Brønsted-Lowry acid centers in pores thereof, by simply adding thereto a modifying metal heterocation, such as $Fe^+$. This step will incorporate Lewis acid centers into the pores. Another effective approach, particularly useful where the starting catalyst is an aluminosilicate microporous material, is to treat the catalyst with steam at a temperature sufficient to cause dealumination of the structure within the micropores. The result of this dealumination is formation of Lewis acid centers in the micropores. It is generally within the understanding of those skilled in the art that suitable catalysts may display different amounts and strengths of Brønsted-Lowry-type and/or Lewis-type acidity on the same surface, depending upon the composition and structure of the catalyst, as well as the method of any given catalyst's preparation and any post-synthesis treatment(s) it may receive. The strength and the ratio of Lewis acid centers to Brønsted-Lowry acid centers will often affect the conversion and distribution of the obtained oxygenate products. For example, increasing the strength of both Lewis acid and Brønsted-Lowry acid sites leads to a progressive increase in alkane conversion, i.e., yield, of oxygenate products in general, while the selectivity to specific products may be varied by altering the ratio of Lewis acid centers to Brønsted-Lowry acid centers.

As noted hereinabove, the selected catalyst is capable of providing confinement of the $C_1$-$C_8$ hydrocarbon molecules being oxidized. The term "confinement" as used herein means that the catalyst has a structure including pores, and that the pore dimensions are capable of at least partially admitting and holding (i.e., "confining") the selected $C_1$-$C_8$ hydrocarbon molecules, thereby altering the admitted molecules' structure and reactivity in some way. Another way of stating this is that the critical diameter of the selected $C_1$-$C_8$ hydrocarbon molecule is smaller than the average cross-sectional diameter of the pores. These pores may be micropores, having a diameter less than 2 nanometers (nm); mesopores, having a diameter from 2 nm to 50 nm; and/or macropores, having a diameter greater than 50 nm; with the characterization of a catalyst as being microporous, mesoporous, or macroporous being based on its predominant average pore diameter. In certain particular embodiments the catalyst is a molecular sieve, i.e., a microporous solid material, and preferably a molecular sieve including silicon (Si) and oxygen (O), for example, in the form of an oxide of silicon, i.e., silicon dioxide ("silica," $SiO_2$). Such molecular sieve may also include, in its structure and not as a modifying metal or modifying metal oxide, aluminum (Al), for example, in the form of an oxide of aluminum, e.g., aluminum oxide ("alumina," $Al_2O_3$). Where both silica and alumina are present, the result is an aluminosilicate molecular sieve, which is also called a zeolite. Such may be naturally-occurring or synthetic, having a structure defined by the International Zeolite Association. Of particular effect may be those having a structure defined as an "MFI" type, such as those designated with the "ZSM" prefix, and of these the zeolite designated as "ZSM-5" may in some embodiments be preferred. The selected material may have a wide range of ratios of $SiO_2/Al_2O_3$, ranging from 20 to 10,000. Other materials characterized as zeolites or zeotypes (i.e., artificial structures synthesized to correspond to defined zeolite structures), including but not limited to those having a beta structure, a mordenite structure, a ferrierite structure, a faujasite structure, a rho structure, or a chabazite structure, and combinations of such materials, may also be useful in the inventive process, provided such contain both Brønsted-Lowry and Lewis acid centers as described hereinabove. Further non-limiting examples include a variety of other zeolites, such as Zeolite-Y, Zeolite Beta (Zeolite-β), and Ferrierite.

The catalyst structure may be crystalline, amorphous, or a combination thereof, and may also include a relatively small amount of a modifying metal and/or a modifying metal oxide. Such modifying metal and/or modifying metal oxide is, by definition, different from any metals included in the primary structure of the catalyst, and may be selected from aluminum (Al), gallium (Ga), iron (Fe), zinc (Zn), copper (Cu), titanium (Ti), and phosphorus (P); oxides thereof; and combinations thereof; in an amount ranging from 10 parts per million (ppm), i.e., a trace amount, to 10% by weight (wt %), based on the total weight of the catalyst. In preferred embodiments the amount may range from 1 wt % to 5 wt %, on the same basis. Thus, in one embodiment the catalyst may have a microporous crystalline aluminosilicate structure, further including a modifying metal or metal oxide other than Al or $Al_2O_3$, while in another embodiment the catalyst may have a silicate structure, and include a modifying metal or metal oxide such as, in non-limiting examples, Al, $Al_2O_3$, Ga, Fe, CuO or $Cu_2O$. Preferred catalysts may include iron modified representatives of the ZSM-5 zeolite, e.g., those including from 10 ppm to 10 wt % of iron, based on the weight of the ZSM-5 zeolite.

The catalyst may be either supported or unsupported, or may serve simultaneously as both catalyst and support, and may be formed by a variety of methods. For example, in unsupported form the catalyst may be used as a crystalline or amorphous powder. Where a supported catalyst is desired, the catalyst may be combined with a binder into an extrudate or pellets for added strength and durability; may be deposited on or in a support material; or may be formed as a membrane. Support materials may be selected from, for example, ceramic materials, defined as inorganic non-metallic solids prepared by heating followed by cooling, including but not limited to oxides, such as zirconia; non-oxides such as carbides, nitrides, borides and silicides; other solids such as metals and alloys, for example, materials based on carbon, nickel, cobalt, molybdenum, and stainless steels; and combinations thereof. In certain embodiments, where a gas stream such as $CH_4$ or $C_2H_6$ is to be oxidized, it may be particularly convenient to use a solid, supported catalyst.

The catalyst may be synthesized and/or modified, via post-synthesis treatment, by a method selected from, for example, hydrothermal synthesis, impregnation, deposition-precipitation, sol immobilization, sublimation, chemical vapor infiltration, or a combination thereof. In one embodiment it may be desirable to calcine the catalyst after it has been prepared, in order to increase its activity; in another embodiment it may be useful to reduce the catalyst with hydrogen; and in a third embodiment it may be useful to treat the catalyst in water vapor, e.g., steam, which may increase its selectivity to a desired target alcohol product. When the catalyst has been prepared by chemical vapor infiltration, washing the catalyst with acetone or an acid following preparation may desirably improve its activity and/or selectivity.

Synthetic zeolites useful in the inventive process may be prepared by slow crystallization of, in one embodiment, a silica-alumina gel in the presence of an alkali and an organic template. The product properties depend upon reaction mixture composition, pH of the system, operating temperature, pre-reaction and reaction times, and template used. One such process is a sol-gel method. In that method, other elements, including, for example, modifying metals and/or modifying metal oxides, may be conveniently incorporated in the zeolite structure. A calcination pre-treatment (i.e., post-synthesis, but prior to use in the inventive process), at a temperature from 200° C. to 800° C., preferably from 400° C. to 700° C., to increase the activity and/or alter the selectivity of the final catalyst prior to using it, may be particularly useful for zeolites. Such pre-treatment may be performed in a static or flow procedure in a diluent selected from air, $H_2$, an inert gas, and combinations thereof. Water vapor may optionally be included with the diluent.

In certain embodiments of the inventive process it may be desirable to use a combination of two different catalysts, with one catalyst being selected for its catalytic effect predominantly in the reaction between a hydrogen source and an oxygen source to form $H_2O_2$, and the other catalyst being selected for its catalytic effect predominantly in the reaction between the $C_1$-$C_8$ hydrocarbon and the $H_2O_2$ to form the target oxygenate product(s). For example, heterogeneous gold-palladium (Au—Pd) catalysts prepared on a support (for example, titanium dioxide ($TiO_2$) or carbon (C)) may be used to produce $H_2O_2$ in a pressurized autoclave wherein $H_2$ and $O_2$ are contacted in aqueous solution, while an iron modified ZSM-5 (Fe/ZSM-5) catalyst, also present in the same solution, utilizes the formed $H_2O_2$ to oxidize the $C_1$-$C_8$ hydrocarbon, e.g., $C_2H_6$, present in solution. See, for example, G. J. Hutchings, et al., *Science*, 323 (2009), 5917, 1037-1041. In certain other embodiments it may be desirable to use a single catalyst capable of effecting both reactions. For example, a supported heterogeneous catalyst prepared by depositing Au—Pd nanoparticles on ZSM-5 (or Fe/ZSM-5) catalyst, wherein the ZSM-5 (or the Fe/ZSM-5) serves in part as the support for the Au—Pd nanoparticles, may be effective to generate $H_2O_2$ in the Au—Pd nanoparticles. This $H_2O_2$ may then be used by sites present in the ZSM-5 (or the Fe/ZSM-5) support to oxidize the $C_1$-$C_8$ hydrocarbon, e.g., $CH_4$, to the corresponding partially oxygenated product.

The inventive process includes contacting the selected $C_1$-$C_8$ hydrocarbon and the $H_2O_2$. In order to do this, in one non-limiting embodiment the hydrocarbon may be fed, with or without a diluent, in gas phase or condensed phase (condensed phase being, accordingly, a solid, a combination of a solid and a liquid, e.g., a dispersion or slurry, or a combination of a gas and a liquid, e.g., an aerosol), to a reaction vessel containing the heterogeneous catalyst. There the heterogeneous catalyst, for example, an iron-modified ZSM-5 zeolite, activates the $C_1$-$C_8$ hydrocarbon and $H_2O_2$ mixture to form one or more corresponding at least partially oxidized products ("oxygenate products"). Such products may include, for example, an alcohol that corresponds to, i.e., has the same number of carbon atoms as, the starting $C_1$-$C_8$ hydrocarbon. In certain embodiments the reaction may be maintained at a temperature preferably from 0° C. to 200° C., more preferably from 10° C. to 100° C., and most preferably from 30° C. to 90° C. In general, a range from 0° C. to 90° C. may be typically employed. For example, some of the described heterogeneous zeolite catalysts may effectively catalyze the reaction of $CH_4$ and $H_2O_2$ in water to form methanol ($CH_3OH$), using a temperature as low as 2° C., with minimal losses to CO or $CO_2$ as by-products. In certain embodiments the amount of water may range from trace (10 ppm) levels to 50 wt % or higher, and a minimum of 50 wt % of water may be preferred, particularly in condensed phase reactions. Also in particular embodiments, the process may be effectively conducted to maintain a total system pressure ranging from 1 to 140 atm (0.101 MPa to 14.19 MPa), more preferably from 8 to 100 atm (0.81 to 10.13 MPa), and most preferably from 20 to 70 atm (2.03 to 7.09 MPa). Moreover, it may be desirable that the process can be conducted such that, where the $C_1$-$C_8$ hydrocarbon is not entirely in solution, any amount thereof that is in gas phase is maintained within a similar pressure range. In one particular embodiment, the process may be carried out entirely in gas phase, as either a continuous or cyclic process.

The amount of hydrogen peroxide that is used to react with the selected $C_1$-$C_8$ hydrocarbon is preferably effective to at least partially oxidize the hydrocarbon to its corresponding target oxygenate product(s). Typically the amount of hydrogen peroxide used is sufficient to maximize the amount of the $C_1$-$C_8$ hydrocarbon being oxidized to its corresponding target oxygenate product, without over-oxidation thereof. Thus, where an alcohol is the target oxygenate product, it is desirable to avoid or minimize production of the corresponding more-oxidized products, such as the corresponding alkyl peroxide, aldehyde, and/or carboxylic acid. Where the $H_2O_2$ is to be generated in situ, any amounts of the hydrogen source and the oxygen source may be employed, provided that the amounts are sufficient to produce hydrogen peroxide in the desired quantity to achieve the desired conversion of the $C_1$-$C_8$ hydrocarbon. The in situ hydrogen peroxide may be generated through the use of a suitable heterogeneous catalyst in the liquid phase. By "in situ" it is meant that the hydrogen peroxide is produced within the reactor simultaneously with the oxidation of the $C_1$-$C_8$ hydrocarbon. For example, in one embodiment a selected closed reactor vessel is charged with an aqueous medium including a suitable heterogeneous catalyst. An $H_2/O_2$ gas mixture may be combined with a $CH_4$ stream, and optionally a diluent, and then pressurized to a level as previously defined. The ratio of $H_2:O_2$ employed preferably ranges from 1:5 to 5:1; more preferably from 1:3 to 3:1; and most preferably from 1:2 to 2:1. Those skilled in the art will be aware that it is advisable to ensure that the $H_2:O_2$ ratios and $C_1$-$C_8$ hydrocarbon and diluent pressures are selected to avoid potentially explosive combinations.

Following formation of the desired target oxygenate product or mixture of products, appropriate separation steps may be carried out where necessary. Standard separation means and methods may be employed. Where the catalyst or combination of catalysts is/are solid and insoluble in either liquid or gas phase, such may be conveniently separated using simple filtration, and optionally then appropriately regenerated and/or recycled back into the same or a different reaction process. Regeneration steps may include, for example, burning off any build-up on the catalyst or treating the catalyst with a fresh hydrogen peroxide solution. The catalyst may also be subjected to such regeneration periodically, according to need. Thus, the process of the invention may be operated as a batch, semi-batch, or continuous process.

EXAMPLES

In the Examples the following are used without further purification: $CH_4$, 99.999% purity; 25% oxygen/carbon dioxide, 99.99% purity; and 5% hydrogen/carbon dioxide. The gas mixture of the reactor is removed using a gas sampling bag and analysis is performed using gas chromatography (GC). Liquid-phase products are analyzed using high performance liquid chromatography (HPLC) or proton nuclear magnetic resonance ($^1$H-NMR). Deuterium oxide ($D_2O$) is used as the lock reference. In the $^1$H-NMR analysis, a sealed capillary tube is prepared with a solution of tetramethylsilane (TMS) and chloroform ($CHCl_3$). $H_2O_2$ yield is determined by titration of aliquots of the final filtered solution with acidified cesium sulphate ($Ce(SO_4)_2$) solutions, which have been standardized against hydrated ammonium ferrosulphate $(NH_4)_2Fe(SO_4)_2.6H_2O$ using ferroin as the indicator. The zeolite catalyst is synthesized using tetraethyl orthosilicate (99.999% trace metal basis), tetrapropylammonium hydroxide (20 wt % in water) and hydrated iron nitrate ($Fe(NO_3)_3.9H_2O$) (purity greater than 98%), all available from Sigma Aldrich. Commercially available catalysts include Zeolite ZSM-5, Zeolite Beta (Zeolite-β), and Ferrierite, obtained from Zeolyst International; and Zeolite-Y, available from P.Q. Zeolites, B.V. Samples of Zeolite ZSM-5 are calcined in static air at 600° C. prior to use in the Examples. A parenthetical number immediately following the zeolite name, e.g., "(30)," indicates the molar ratio of $SiO_2/Al_2O_3$ as provided by the supplier. Copper acetylacetonate ($Cu(C_5H_7O_2)_2$) and iron acetylacetonate ($Fe(C_5H_7O_2)_3$) have a purity greater than 99.95% and are supplied by Sigma Aldrich. Silica-alumina grade 135 catalyst support is also supplied by Sigma Aldrich (6 wt % Al content).

Catalyst Preparations:

(A) Preparation of Silicalite-1 (Mole Ratio of Template: Si=1.0) Catalyst/Catalyst Support.

Silicalite-1 is prepared as follows. Tetraethyl orthosilicate (10.3 grams (g), 49.4 millimoles (mmoles)) is stirred vigorously at 25° C. for one hour (h). To this, a 20 wt % solution of tetrapropylammonium hydroxide (TPAOH) (50.8 g, corresponding to 10.16 g TPAOH, 49.9 mmoles) is added dropwise with vigorous stirring at 25° C. The clear gel is vigorously stirred at 25° C. for a further hour, and later for 5 h at 60° C. The resulting gel is heated in a Teflon™-lined stainless steel autoclave at 175° C. for 48 hours. (Teflon™ is a trademark of E.I. du Pont de Nemours, Inc.) The materials are recovered by filtration, washed with deionized water and dried at 110° C. for 16 h. The dried sample is calcined for 24 h at 550° C. in a flow of air.

(B) Preparation of Fe/Silicalite-1 (Mole Ratio of $SiO_2/Fe_2O_3$=260) Catalyst by a Hydrothermal Method.

Samples of Silicalite-1 with Fe present in the tetrahedral framework positions are prepared as follows. A solution containing $Fe(NO_3)_3.9H_2O$ (0.147 g, 0.38 mmoles) and oxalic acid (0.152 g, 1.25 mmoles) in water (10 milliliters (mL), 10 g, 0.55 moles) is prepared and stirred at room temperature for 20 h. A second solution is then prepared, beginning with stirring tetraethyl orthosilicate (10.24 g, 49.4 mmoles) vigorously at 25° C. for 1 h. To this, a 20 wt % solution of TPAOH (15.0 g, corresponding to 3.0 g TPAOH, 15.4 mmoles) is added dropwise with vigorous stirring at 25° C. The clear gel is subsequently stirred at 25° C. for 3 h. The original solution containing iron nitrate and oxalic acid is then added dropwise with vigorous stirring to obtain a homogeneous clear gel with the proportional molar composition, based on $SiO_2$=1; $Fe_2O_3$, 0.00385; $H_2C_2O_4$, 0.013; TPAOH, 0.312; and $H_2O$, amount unknown. The resulting gel is homogenized over 3 h, and later crystallized in a Teflon™-lined stainless steel autoclave at 175° C. for 72 h. The as-synthesized material is recovered by filtration, washed with deionized water and dried at 110° C. for 16 h. The dried sample is then calcined for 8 h at 550° C. in a flow of nitrogen ($N_2$) for 5 h, followed by air for 3 h. Subsequently, the sample is ion-exchanged with a 1.0 molar (M) solution of ammonium nitrate ($NH_4(NO_3)_3$) three times at 85° C., and is finally activated in steam at 550° C. for 3 h.

(C) Preparation of a Fe/ZSM-5 (30) Catalyst by Chemical Vapor Infiltration (CVI).

Fe/ZSM-5 (30) catalyst is prepared by CVI as follows. A 1-g sample of commercially obtained ZSM-5 (30) zeolite is treated under vacuum for 2 h. A commercial sample of iron acetylacetonate ($Fe(C_5H_7O_2)_3$ (0.0774 g), corresponding to a nominal final metal loading of 1.1 wt %, is then mixed with the vacuum-treated ZSM-5 zeolite. The mixture is placed under vacuum and heated to 150° C. for 2 h. The material is then removed and calcined in air at 400° C. for 3 h.

(D) Preparation of an Acetone Washed Fe/ZSM-5 (30) Catalyst by CVI.

Fe/ZSM-5 (30) catalyst is prepared as follows. An amount of the commercial ZSM-5 (30) (1 g) is treated under vacuum for 2 h. Then $Fe(C_5H_7O_2)_3$ (0.1760 g), corresponding to a nominal final metal loading of 2.5 wt %, is manually mixed with the pre-treated ZSM-5 catalyst. The mixture is placed under vacuum and heated to 150° C. for 2 h, then removed from the vacuum chamber and washed with acetone (500 mL), filtered and air dried. It is then calcined in air at 400° C. for 3 h. This process removes some of the deposited iron metal from the sample.

(E) Preparation of a Cu/ZSM-5 (30) Catalyst by CVI.

Cu/ZSM-5 (30) catalyst is prepared as follows. An amount of commercial ZSM-5 (30) (1 g) is treated under vacuum for 2 h. Copper acetylacetonate ($Cu(C_5H_7O_2)_2$) (0.1030 g), corresponding to a nominal final metal loading of 2.5 wt %, is then manually mixed with the pre-treated ZSM-5. The mixture is put under vacuum and heated to 150° C. for 2 h. The material is then removed and calcined in air at 400° C. for 3 h.

(F) Preparation of a $Fe/SiO_2.Al_2O_3$ Catalyst by CVI.

$Fe/SiO_2.Al_2O_3$ catalyst is prepared as follows. An amount of $SiO_2$—$Al_2O_3$ (1 g) is treated under vacuum for 2 h. $Fe(C_5H_7O_2)_3$ (0.1760 g), corresponding to a nominal metal loading of 2.5 wt %, is manually mixed with the pre-treated $SiO_2.Al_2O_3$. The mixture is put under vacuum and heated to 150° C. for 2 h. The material is then removed and calcined in air at 400° C. for 3 h.

(G) Preparation of a Fe/Ferrierite Catalyst by CVI.

Fe/Ferrierite catalyst is prepared as follows. An amount of ferrierite ($SiO_2/Al_2O_3=20$) (1 g) is treated under vacuum for 2 h. $Fe(C_5H_7O_2)_3$ (0.1760 g), corresponding to a nominal metal loading of 2.5 wt %, is manually mixed with pre-treated Ferrierite. The mixture is put under vacuum and heated to 150° C. for 2 h. The material is then removed and calcined in air at 550° C. for 3 h.

(H) Preparation of a Fe/Silicalite-1 Catalyst by CVI.

Fe-Silicalite-1 catalyst is prepared as follows. An amount of the Silicalite-1 (made by hydrothermal synthesis as described in Preparation (A)) (0.5 g) is treated under vacuum for 2 h. $Fe(C_5H_7O_2)_3$ (0.088 g), corresponding to a nominal metal loading of 2.5 wt %, is manually mixed with the pre-treated Silicalite-1. The mixture is placed under vacuum and heated to 150° C. for 2 h. The material is then removed and calcined in air at 550° C. for 3 h.

Examples 1-3

Liquid Phase Oxidation of $CH_4$ with $H_2O_2$ Using a ZSM-5 (30) Catalyst at Several Temperatures Catalytic oxidation of $CH_4$ is carried out using a stainless-steel autoclave (Parr reactor) containing a Teflon™-lined vessel with a total volume of 50 mL. A measured amount of ZSM-5 zeolite (0.028 g) is charged to the vessel, which has already been charged with a 10-mL solution of distilled water and an amount of $H_2O_2$ (50 wt %, 0.005 mol). The total volume of the reaction solution is 10 mL. Air in the reactor is removed by purging 3 times with $CH_4$ at 200 pounds per square inch (psi) (13.61 bar, 1.37 MPa), and then the system is pressurized with $CH_4$ to a fixed pressure (440 psi, 3.03 MPa, 0.03 mol). In separate runs, the autoclave is heated to 30° C., 50° C., and 80° C., respectively. Once each respective reaction temperature is attained, the solution is vigorously stirred at 1500 revolutions per minute (rpm) and maintained at the reaction temperature for 0.5 h to enable completion of each respective oxidation reaction. At the end of the reaction the autoclave is cooled with ice to a temperature of 12° C. to minimize the methanol volatility and loss. Products of the reaction are subsequently analyzed and results are shown in Table 1.

Examples 4-5

Liquid Phase Oxidation of $CH_4$ with $H_2O_2$ Using a ZSM-5 (30) Catalyst at Several Pressures Catalytic oxidation of $CH_4$ is carried out as in Example 2, i.e., temperature at 50° C., but using pressures of 5.1 bar (0.51 MPa) and 15.3 bar (1.53 MPa), respectively. Products are subsequently analyzed and results are shown in Table 1.

Examples 6-7

Liquid Phase Oxidation of $CH_4$ with $H_2O_2$ Using a ZSM-5 (30) Catalyst at Several Concentrations of $H_2O_2$ Catalytic oxidation of $CH_4$ is carried out as in Example 2, but using hydrogen peroxide concentrations corresponding to 0.99 M and 0.10 M, respectively. Products are subsequently analyzed and results are shown in Table 1.

Examples 8-9

Liquid Phase Oxidation of $CH_4$ with $H_2O_2$ Using a ZSM-5 Catalyst at Several $SiO_2/Al_2O_3$ Ratios Catalytic oxidation of $CH_4$ is carried out as in Example 2, but using commercial ZSM-5 samples that contain various amounts of aluminum (Al), which are 1.3 wt % and 2.7 wt %, respectively. The ZSM-5 samples are described as having $SiO_2/Al_2O_3$ of 50 and 23, respectively. Products are subsequently analyzed and results are shown in Table 1.

Example 10

Liquid Phase Oxidation of $CH_4$ with $H_2O_2$ Using ZSM-5 (30) Catalyst After High Temperature Steaming Catalytic oxidation of $CH_4$ is carried out as in Example 2, but using commercial ZSM-5 samples that have been pre-treated with steam (water vapor 10% by volume) at 600° C. for 3 h. Products are subsequently analyzed and results are shown in Table 1.

Examples 11

Liquid Phase Oxidation of $CH_4$ with $H_2O_2$ Using Zeolite-β

Catalytic oxidation of $CH_4$ is carried out as in Example 2, but using Zeolite-β ($SiO_2/Al_2O_3$=38) as the catalyst. The catalyst is calcined at 600° C. in static air for 3 h prior to use. Products are subsequently analyzed and results are shown in Table 1.

Example 12

Liquid Phase Oxidation of $CH_4$ with $H_2O_2$ Using a Fe/ZSM-5 (30) Catalyst Steam-Treated at 550° C.

The oxidation process of Example 2 is repeated with the following modifications. Fresh Fe/ZSM-5 catalyst prepared by CVI as in preparation (C) is calcined at 550° C. for 3 h in flowing air in the presence of water vapor before use in the reaction. The remainder of processing is the same as in Example 2. Products are subsequently analyzed and results are shown in Table 1.

Example 13

Liquid Phase Oxidation of $CH_4$ with $H_2O_2$ Using a Calcined Cu/ZSM-5 (30) Catalyst Catalytic oxidation of $CH_4$ is carried out using the procedure of Examples 2 and the catalyst of Preparation (E). Products are subsequently analyzed and results are shown in Table 1. This catalyst shows high oxygenate selectivity and increased selectivity to methanol in particular.

Example 14

Liquid Phase Oxidation of $CH_4$ with $H_2O_2$ Using a Calcined Fe/$SiO_2$.$Al_2O_3$ The oxidation process of Example 2 is repeated using fresh catalyst prepared according to Preparation (F). Products are subsequently analyzed and results are shown in Table 1.

Example 15

Liquid Phase Oxidation of $CH_4$ with $H_2O_2$ Using a Calcined Fe/Ferrierite Catalyst Catalytic oxidation of $CH_4$ is carried out using the procedure of Examples 2 and the catalyst of Preparation (G). Products are subsequently analyzed and results are shown in Table 1.

Example 16

Liquid Phase Oxidation of $CH_4$ with $H_2O_2$ Using a Calcined Fe/Silicalite-1 Catalyst Prepared by CVI Catalytic oxidation of $CH_4$ is carried out using the procedure of Example 2 and the catalyst of Preparation (H). Products are subsequently analyzed and results are shown in Table 1.

Example 17

Liquid Phase Oxidation of $CH_4$ with $H_2O_2$ Using a Steamed Fe/Silicalite-1 Catalyst Prepared by a Hydrothermal Method Catalytic oxidation of $CH_4$ is carried out using the procedure of Example 2 and the catalyst of Preparation (B). Products are subsequently analyzed and results are shown in Table 1.

Examples 18

Liquid Phase Oxidation of $C_2H_6$ with $H_2O_2$ Using ZSM-5 (30) Catalyst

Catalytic oxidation is carried out as in Example 2, but using $C_2H_6$ instead of $CH_4$. Products are subsequently analyzed and the results are shown in Table 2.

Example 19

Liquid Phase Oxidation of $C_2H_6$ with $H_2O_2$ Using an Acetone Washed Fe/ZSM-5 (30) Catalyst Catalytic oxidation of $C_2H_6$ is carried out using the procedure of Example 18 using the catalyst of Preparation (D). Products are subsequently analyzed and results are shown in Table 2.

TABLE 1

Activity and effect of reaction conditions on methane oxidation with several catalysts.

| | | Reaction conditions | | | Product amount (μmol) | | | | Oxygenate | Oxygenate |
| --- | --- | --- | --- | --- | --- | --- | --- | --- | --- | --- |
| Example | Catalyst [f] | T, ° C. | P, bar | [$H_2O_2$] (M) | MeOH [a] | HCOOH [a] | MeOOH [a] | $CO_2$ (g) [b] | productivity [c] | selectivity (%) |
| E1 | ZSM-5 (30) [d] | 30 | 30.5 | 0.5 | 8.8 | 13.2 | 12.6 | 1.4 | 2.6 | 96 |
| E2 | ZSM-5 (30) [d] | 50 | 30.5 | 0.5 | 15.4 | 44.0 | 17.7 | 4.4 | 5.6 | 95 |
| E3 | ZSM-5 (30) [d] | 80 | 30.5 | 0.5 | 19.9 | 195.8 | 11.8 | 54.6 | 16.9 | 81 |
| E4 | ZSM-5 (30) [d] | 50 | 5.1 | 0.5 | 9.0 | 26.6 | 13.4 | 3.5 | 3.7 | 93 |
| E5 | ZSM-5 (30) [d] | 50 | 15.3 | 0.5 | 9.0 | 21.7 | 13.3 | 2.3 | 3.3 | 95 |
| E6 | ZSM-5 (30) [e] | 50 | 30.5 | 0.99 | 25.6 | 52.4 | 31.4 | 3.4 | 8.1 | 97 |
| E7 | ZSM-5 (30) [e] | 50 | 30.5 | 0.10 | 1.3 | 4.4 | 2.2 | 0.1 | 0.6 | 99 |
| E8 | ZSM-5 (50) [d] | 50 | 30.5 | 0.5 | 9.0 | 18.5 | 9.2 | 0.9 | 2.7 | 98 |
| E9 | ZSM-5 (23) [d] | 50 | 30.5 | 0.5 | 6.1 | 2.0 | 14.0 | 0.7 | 1.7 | 97 |
| E10 | ZSM-5 (30) steamed | 50 | 30.5 | 0.5 | 25.7 | 59.1 | 14.8 | 6.5 | 7.2 | 94 |
| E11 | Beta (38) [d] | 50 | 30.5 | 0.5 | 1.3 | 0.4 | 1.7 | 1.1 | 0.3 | 75 |
| E12 | Fe/ZSM-5 (30) CVI steamed | 50 | 30.5 | 0.5 | 40.7 | 303.9 | 0.0 | 59.9 | 24.6 | 90 |
| E13 | Cu/ZSM-5 (30) CVI | 50 | 30.5 | 0.5 | 103.9 | 0.0 | 2.6 | 10.1 | 7.6 | 91 |
| E14 | Fe/$SiO_2$•$Al_2O_3$ CVI | 50 | 30.5 | 0.5 | 1.0 | 0.0 | 3.9 | 0.9 | 0.4 | 84 |

TABLE 1-continued

Activity and effect of reaction conditions on methane oxidation with several catalysts.

| | | Reaction conditions | | | Product amount (μmol) | | | | Oxygenate productivity [c] | Oxygenate selectivity (%) |
|---|---|---|---|---|---|---|---|---|---|---|
| Example | Catalyst [f] | T, °C. | P, bar | [$H_2O_2$] (M) | MeOH [a] | HCOOH [a] | MeOOH [a] | $CO_2$ (g) [b] | | |
| E15 | Fe/Ferrierite CVI | 50 | 30.5 | 0.5 | 7.7 | 2.5 | 11.8 | 3.9 | 1.6 | 85 |
| E16 | Fe/Silicalite-1 CVI | 50 | 30.5 | 0.5 | 2.6 | 2.2 | 2.4 | 0.1 | 0.3 | 99 |
| E17 | Fe/Silicalite-1 hydrothermal synthesis, steamed | 50 | 30.5 | 0.5 | 28.8 | 113.5 | 9.2 | 14.6 | 10.8 | 91 |

Reaction conditions: Catalyst: various (28 mg); $P_{(CH4)}$: 30.5 bar (3.05 MPa); time: 30 min; rpm: 1500.
[a] = analyzed by $^1$H-NMR with 1% TMS in deuterated chloroform ($CDCl_3$) as the internal standard
[b] = analyzed by gas chromatograph with flame ionization detector (GC-FID); values obtained based on $CO_2$ calibration curve
[c] = calculated as "moles (oxy) $kg^{-1}$ (cat) $h^{-1}$"
[d] = catalyst calcined at 600° C. in static air for 3 h before use
[e] = catalyst calcined at 500° C. in static air for 3 h before use
[f] = the number between brackets following the label "ZSM-5" or Beta indicates the $SiO_2/Al_2O_3$ ratio as given by the provider (Zeolyst). Experimental values obtained by neutron activation analysis (NAA) by The Dow Chemical Company are 1.3, 2.0 and 2.7 Al wt % for ZSM-5 catalysts (50), (30) and (23), respectively.

TABLE 2

Ethane oxidation with two catalysts.

| | | Product amount (μmol) | | | | | Oxygenate productivity [c] | Oxygenate selectivity (%) |
|---|---|---|---|---|---|---|---|---|
| Example | Catalyst | C1-C2 alcohols [a] | C1-C2 acids [a] | Other oxygenates [a] | CO + $CO_2$ (g) [b] | $C_2H_4$ (g) [b] | | |
| E18 | ZSM-5 (30) [d] | 72.0 | 157.1 | 17.0 | 8.2 | 0 | 17.6 | 96.7 |
| E19 | Fe/ZSM-5 (30) CVI Acetone-washed | 306.2 | 768.1 | 7.76 | 18.5 | 25.2 | 80.4 | 96.1 |

Reaction conditions: Catalyst: various (28 mg); $P_{(C2H6)}$: 30.5 bar (3.05 MPa); time: 30 min; rpm: 1500.
[a] = analyzed by $^1$H-NMR with 1% TMS in $CDCl_3$ as the internal standard
[b] = analyzed by GC-FID; values based on $CO_2$ calibration curve
[c] = calculated as "moles (oxy) $kg^{-1}$ (cat) $h^{-1}$"
[d] = ZSM-5 calcined at 600° C. in static air for 3 h

What is claimed is:

1. A process for the partial oxidation of hydrocarbons, comprising contacting a $C_1$-$C_2$ saturated hydrocarbon and hydrogen peroxide in the presence of a molecular sieve catalyst under suitable conditions to convert the saturated $C_1$-$C_2$ hydrocarbon to at least one corresponding $C_1$-$C_2$ partial oxygenate product, wherein the molecular sieve catalyst provides confinement in micropores having an average cross-sectional diameter of less than two nanometers, such cross-sectional diameter being greater than the critical diameter of the $C_1$-$C_2$ saturated hydrocarbon, and the molecular sieve catalyst having a structure containing Brønsted-Lowry acid centers and the molecular sieve catalyst further including at least one coordinatively-unsaturated cation that is not incorporated into the structure of the molecular sieve catalyst, such cation being of a modifying metal or metal oxide species selected from the group consisting of iron (Fe), copper (Cu),-oxides thereof, and combinations thereof, and wherein the molecular sieve catalyst is a zeolite having an MFI structure, a beta structure, or a ferrierite structure, with a $SiO_2/Al_2O_3$ ratio ranging from 20 to 10,000.

2. The process of claim 1, wherein the conditions include a temperature from 0° C. to 90° C.

3. The process of claim 1, wherein the conditions include a total system pressure of from 1 to 140 standard atmospheres (0.1 MPa to 14 MPa).

4. The process of claim 1, wherein the conditions include the $C_1$-$C_2$ hydrocarbon and the hydrogen peroxide being in a phase selected from (a) a condensed phase; (b) a gas phase; and (c) a combination thereof.

5. The process of claim 1, wherein the catalyst includes in its structure silicon (Si) and oxygen (O).

6. The process of claim 1, wherein the catalyst includes in its structure, an oxide of aluminum, or an oxide of aluminum and an oxide of silicon, and is crystalline, amorphous, or a combination thereof.

7. The process of claim 1, wherein the modifying metal or modifying metal oxide is in an amount from 10 parts per million to 10 weight percent, based on total weight of the catalyst.

8. The process of claim 1, wherein the catalyst is pre-treated, prior to use in the process, by heating at a temperature from 200° C. and 800° C. under conditions such that activity of the pre-treated catalyst is increased in comparison with an otherwise identical catalyst that has not been pre-treated.

9. The process of claim 1, wherein the hydrogen peroxide is provided at the beginning of the reaction in aqueous solution; or is generated in situ by contacting hydrogen and oxygen in the presence of a suitable heterogeneous catalyst to form the hydrogen peroxide; or both.

* * * * *